(12) United States Patent
Matalon

(10) Patent No.: US 8,440,182 B2
(45) Date of Patent: May 14, 2013

(54) METHODS AND COMPOSITIONS FOR TREATING PHENYLKETONURIA

(75) Inventor: Reuben Matalon, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 476 days.

(21) Appl. No.: 12/592,244

(22) Filed: Nov. 20, 2009

(65) Prior Publication Data

US 2011/0123573 A1 May 26, 2011

Related U.S. Application Data

(63) Continuation of application No. PCT/US2008/006655, filed on May 23, 2008.

(60) Provisional application No. 60/931,645, filed on May 24, 2007.

(51) Int. Cl.
*A61K 9/00* (2006.01)
*A61K 38/43* (2006.01)
*A61K 38/51* (2006.01)
*A61K 38/48* (2006.01)

(52) U.S. Cl.
USPC .......... 424/94.1; 424/94.5; 424/94.63

(58) Field of Classification Search .......... 424/400, 424/94.1, 94.5, 94.63
See application file for complete search history.

(56) References Cited

FOREIGN PATENT DOCUMENTS

| | | | |
|---|---|---|---|
| JP | WO 85/03230 A1 | 8/1985 | |
| WO | WO 2006/004719 A2 | 1/2006 | |

OTHER PUBLICATIONS

Kim et al. Trends in enzyme therapy for phenylketonuria. Mol. Therapy 10(2), pp. 220-224 (2004).*
Iwaki et al. Proteolytic modification of the amino-terminal and carboxyl-terminal regions of rat hepatic phenylalanine hydroxylase. J. Biol. Chem. 261(5), pp. 2051-2056 (1986).*
Doskeland, A.P., et al., "Phosphorylation of Recombinant Human Phenylalanine Hydroxylase: Effect on Catalytic Activity, Substrate Activation and Protection Against Non-Specific Cleavage of the Fusion Protein by Restriction Protease", The Biochemical Journal, 1996, pp. 409-414, vol. 313.
Gamez, Alejandra et al., "Toward PKU enzyme replacement therapy: PEGylation with activity retentions for three forms of recombinant phenylalanine hydroxylase", Molecular Therapy: The Journal of the American Society of Gene Therapy, 2004, pp. 124-129, vol. 9(1).
Hoskins, J.A., "Enzymatic Control of Phenylalanine Intake in Phenylketonuria", The Lancet, 1980, pp. 392-394, vol. 1(8165).
Jia, X., et al., "A New Strategy of Gene Therapy for Hyperphenylalaninemia Rats", Zhonghua Yi Xue Za Zhi, 2000, pp. 464-467, vol. 80(6).
Kim, W., et al., "Trends in Enzyme Therapy for Phenylketonuria", Molecular Therapy, 2004, pp. 220-224, vol. 10 (2).

* cited by examiner

*Primary Examiner* — Barbara P Badio
*Assistant Examiner* — Sara E Townsley

(57) ABSTRACT

Provided herein are methods for treating a subject suffering from phenylketonuria by administering a phenylalanine hydroxylase ("PAH") and/or a phenylalanine ammonia lyase ("PAL") to the subject under conditions effective to deliver the phenylalanine 4-hydroxylase and/or PAL to the subject's small intestine. Also provided are methods for increasing the therapeutic activity of a phenylalanine 4-hydroxylase by thiolating the phenylalanine 4-hydroxylase. In addition, provided are oral dosage forms that include a phenylalanine 4-hydroxylase and/or a PAL and an enteric coating.

11 Claims, 3 Drawing Sheets

METHODS AND COMPOSITIONS FOR TREATING PHENYLKETONURIA

CROSS-REFERENCE TO RELATED APPLICATIONS

This application is a continuation of and claims the benefit of priority under 35 U.S.C. §120 of international application PCT/US2008/006655, filed May 23, 2008, which claims benefit of priority under 35 U.S.C. §119(e) of provisional application U.S. Ser. No. 60/931,645, filed May 24, 2007, both of which are hereby incorporated by reference in their entirety.

BACKGROUND OF THE INVENTION

1. Field of the Invention

The subject invention is directed generally to methods and materials for treating conditions and disorders associated with phenylalanine metabolism and, more particularly, to methods and materials for treating phenylketonuria.

2. Description of the Related Art

Phenylketonuria (PKU) is hyperaminoacidemia of phenylalanine (Phe) associated with an inborn error of phenylalanine metabolism, mutation of the gene encoding phenylalanine 4-hydroxylase (PAH), which converts phenylalanine to tyrosine. In some cases, an additional metabolic defect occurs in the synthetic pathway of either dihydropteridine or tetrahydrobiopterin (BH4), phenylalanine 4-hydroxylase co-factors, contributing further to the hyperphenylalaninemia (HPA). Whereas a normal plasma phenylalanine level is approximately 0.05 mM (1), untreated "classic" PKU patients have plasma phenylalanine levels above 1 mM, e.g., plasma phenylalanine levels of from about 1 mM to about 2.5 mM or more, and, although treatment with a low-phenylalanine diet has a goal of reducing plasma phenylalanine to below 0.3 mM, this is difficult to attain due to dietary compliance problems. In the United States, about 1 in 10,000 babies are born with PKU.

The excessive levels of plasma phenylalanine observed in PKU combined with the relatively high affinity of phenylalanine for binding sites on carrier protein of the neutral amino acid transport system in the blood-brain barrier (BBB) leads to (i) accumulation phenylalanine Phe and its neurotoxic metabolites, e.g., phenylpyruvate, phenylacetate, phenyllactate, in the brain and (ii) depressed levels of non-phenylalanine neutral amino acids entering the brain, resulting in disturbed brain development and function, since key cerebral pathways of metabolism, e.g., synthesis of neurotransmitters, require precursor amino acids, such as tyrosine. This depression is pronounced for tyrosine, which is low in the plasma supply due to the PKU metabolic error in the enzyme responsible for converting phenylalanine to tyrosine. Current thought is that the neurological deficits of PKU are due predominantly to the depression of levels of non-Phe neutral amino acids entering the brain (2).

Although a diet low in phenylalanine can reduce plasma phenylalanine levels in "classic" PKU below 0.3 mM and ameliorate the mental retardation associated with untreated PKU, dietary compliance can be problematic and can become particularly problematic as PKU patients reach adolescence, leading to a rise in plasma phenylalanine levels and to both loss in intelligence and white matter changes in the brain. In addition to requiring patient compliance, therapies based on dietary restriction also requires that the patient know the level of phenylalanine present in a particular food. Moreover, nutritional deficiencies can also result from phenylalanine-restricted diets.

Alternative treatments have thus been developed. For example, to overcome suspected depletion of the neurotransmitters dopamine and serotonin, PKU patients have been treated with the neurotransmitter precursors tyrosine and tryptophan (3). To reduce influx of phenylalanine into the brain, a supplement of branched chain neutral amino acids containing valine, isoleucine, and leucine, was administered to older PKU patients (4), who reported significant improvement in behavioral deficits. It was proposed that the addition of the neurotransmitter precursors, tyrosine and tryptophan (2) to Berry's supplement (4), should lead to further improvement. However, efficacy of these dietary amino acid supplement treatments has been controversial.

In view of the above, there is a recognized need for methods and compositions for treating phenylketonuria and other conditions and disorders associated with phenylalanine metabolism. Specifically, the prior art is deficient in methods of treating phenylketonuria by administering phenylalanine 4-hydroxylase solely or in combination with one or more other enzymes that improve its activity in metabolizing phenylalanine. The present invention fulfills this long-standing need and desire in the art.

SUMMARY OF THE INVENTION

The present invention is directed to a method for treating a subject suffering from phenylketonuria. The method comprises administering one or more of phenylalanine 4-hydroxylase or a phenylalanine ammonia lyase to the subject under conditions effective to deliver the phenylalanine 4-hydroxylase and/or phenylalanine ammonia lyase to the subject's small intestine. In a related method there is provided a further step of administering a peptidase to the subject under conditions effective to deliver the peptidase to the subject's stomach and/or small intestine.

The present invention also is directed to a method for increasing the therapeutic activity of phenylalanine 4-hydroxylase (PAH) in a subject suffering from phenylketonuria. The method comprises administering one or more of a thiolated recombinant phenylalanine 4-hydroxylase or a phenylalanine ammonia lyase to the subject under conditions effective to deliver the thiloated recombinant phenylalanine 4-hydroxylase and/or phenylalanine ammonia lyase to the subject's small intestine. In a related method, there is provided a further step of administering a peptidase as described supra.

The present invention is directed further to an oral dosage form. The oral dosage form comprises one or more cores comprising one or both of a phenylalanine 4-hydroxylase or a phenylalanine ammonia lyase and an enteric coating on the one or more cores. In a related oral dosage form there is provided a further component comprising peptidase.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
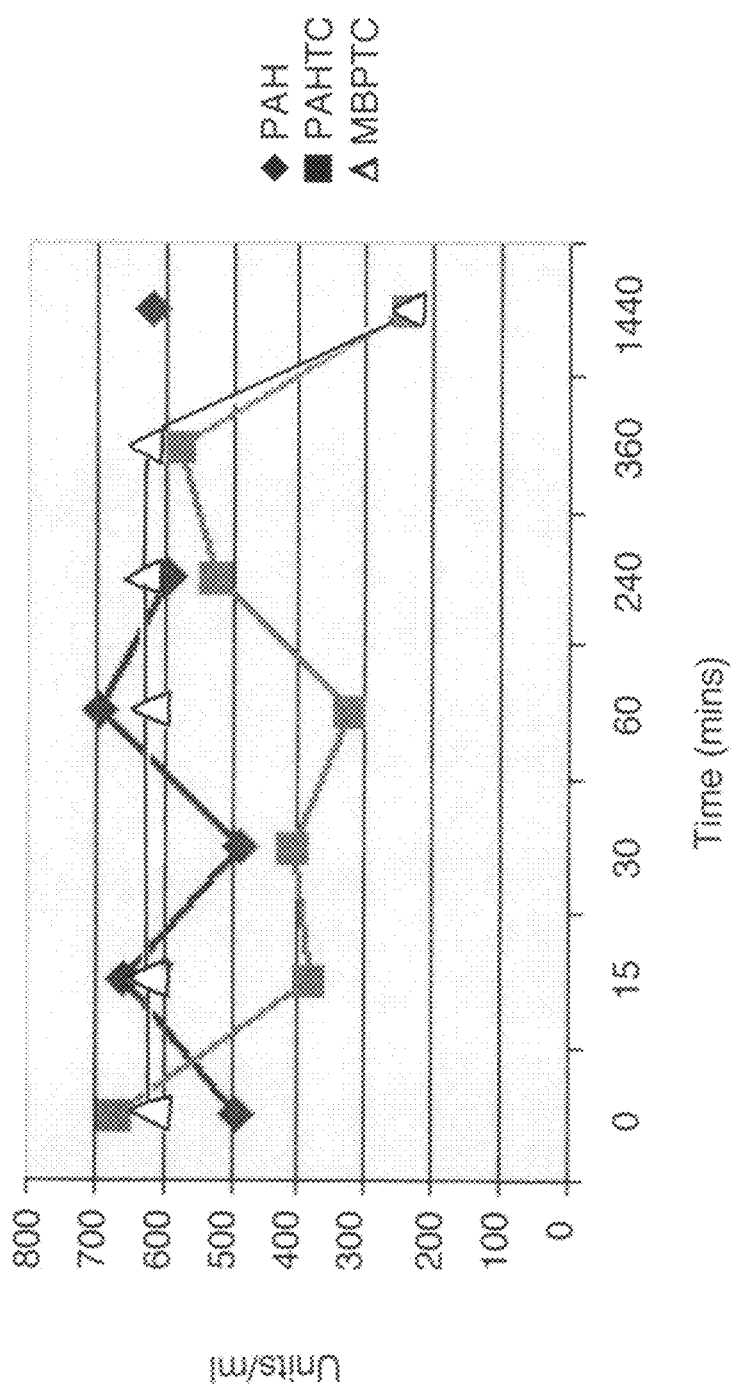
FIG. 1 illustrates graphically the proteolytic digestion of phenylalanine hydroxylase, phenylalanine hydroxylase fused to maltose binding protein and phenylalanine hydroxylase in the presence of trypsin and chymotrypsin.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "PAH" is meant to refer to phenylalanine hydroxylase and to its conjugates that convert phenylalanine to tyrosine. PAH can be "wild-type" phenylalanine 4-hydroxylase, e.g., isolated from natural sources, such as liver tissue, or it can be recombinant phenylalanine 4-hydroxylase, e.g., produced recombinantly by expression in a suitable host, such as $E.$ $coli$. In cases where the phenylalanine 4-hydroxylase is a recombinantly-produced phenylalanine 4-hydroxylase, it can be a recombinantly-produced mouse, human, or other mammalian phenylalanine 4-hydroxylase, e.g., produced recombinantly by expression of a mouse, human, or other mammalian phenylalanine 4-hydroxylase gene in $E.$ $coli$ or other suitable host. The recombinantly-produced phenylalanine 4-hydroxylase can be a full-length phenylalanine 4-hydroxylase, or it can be a truncated phenylalanine 4-hydroxylase, provided, of course, that the truncated phenylalanine 4-hydroxylase retains phenylalanine 4-hydroxylase activity. Alternatively, the recombinantly-produced phenylalanine 4-hydroxylase can be fused or otherwise conjugated to other materials, such as materials that aid in the isolation and/or purification of the recombinantly-produced phenylalanine 4-hydroxylase, for example, as in the case where the recombinantly-produced phenylalanine 4-hydroxylase is fused to maltose binding protein (MBH). In certain embodiments, the recombinantly-produced phenylalanine 4-hydroxylase is one that has been thiolated in a serine/threonine/tyrosine-rich region of the phenylalanine hydroxylase.

As used herein, "serine/threonine/tyrosine-rich region" is meant to refer to a region of the phenylalanine 4-hydroxylase that is rich in serine residues, is rich in threonine residues, is rich in tyrosine residues, and or is rich in any combination of serine, threonine, and tyrosine residues. Illustratively, one such serine/threonine/tyrosine-rich region of phenylalanine 4-hydroxylase is the region near the phenylalanine 4-hydroxylase's serine-16 amino acid residue. Suitable methods for preparing recombinantly-produced phenylalanine 4-hydroxylase and for thiolating such recombinantly-produced phenylalanine 4-hydroxylase in a serine/threonine/tyrosine-rich region include those set forth infra.

As used herein, "PAL" is meant to refer to phenylalanine ammonia lyase and to its conjugates that convert phenylalanine to trans-cinammic acid (e.g., PEGylated PAL).

As used herein, "peptidase" is meant to refer to enzymes that digest proteins and smaller peptide chains into free amino acids and is meant to include proteases. Reference to "peptidase" herein is meant to include one or more peptidases. Examples of suitable peptidases that can be used in the method of the present invention include trypsin, chymotrypsin, and combinations of trypsin and chymotrypsin or one or more dipeptidases.

As used herein, "enteric coating" is meant to include a coating which (i) remains intact for at least 2 hours when in contact with artificial gastric juices such as HCl of pH 1 at 36° C. to 38° C. and (ii) thereafter disintegrates within 30 minutes in artificial intestinal juices such as a $KH_2PO_4$ buffered solution of pH 6.8.

As used herein, "treating" or "treat" is meant to refer to treatment of the direct or indirect cause of a condition, to treatment of a condition's symptoms; or to both. It is contemplated that the effect of such may be whole or partial with respect to the desired outcome.

As used herein, "subject" is meant to refer to any animal, such as any mammal, e.g., mice rats, cats, rabbits, dogs, pigs, horses, cows, and primates, such as humans. Illustratively, "subject", as used herein, is meant to include humans suffering from phenylketonuria, human infants, human children, human adolescents, human adults, male humans, female humans, humans who are less than about 2 years of age, humans who are between about 2 years of age and 5 years of age, humans who are between about 5 and about 10 years of age, humans who are between about 10 and about 18 years of age, humans who are between about 18 and about 30 years of age, humans who are between about 30 and about 40 years of age, humans who are between about 40 and about 50 years of age, humans who are between about 50 and about 60 years of age, humans who are over about 60 years of age. In addition to suffering from phenylketonuria, suitable human subjects include those who are also suffering from tyrosinemia. Suitable human subjects also include those who are also suffering from phenylketonuria, but who are not suffering from tyrosinemia.

In one embodiment of the present invention there is provided a method for treating a subject who has phenylketonuria, the method comprising administering either a phenylalanine 4-hydroxylase and/or a phenylalanine ammonia lyase to the subject under conditions effective to deliver the phenylalanine 4-hydroxylase and/or phenylalanine ammonia lyase to the subject's small intestine.

Further to this embodiment the method comprises administering a peptidase to the subject under conditions effective to deliver the peptidase to the subject's stomach and/or small intestine. The peptidase may be one or more dipeptidase. Also, the peptidase may be administered concurrently or sequentially with one or both of the phenylalanine 4-hydroxylase or phenylalanine ammonia lyase. In addition, the peptidase and one or both of the phenylalanine 4-hydroxylase or phenylalanine ammonia lyase are administered in separate formulations or in a single formulation. The formulations may be enterically coated. Also, the formulations may be formulated for time-release of the peptidase(s) and/or one or both of the phenylalanine 4-hydroxylase or phenylalanine ammonia lyase. Furthermore, one or both of the phenylalanine 4-hydroxylase or the phenylalanine ammonia lyase may be formulated with an enteric coating as a single formulation or separate formulations.

In both embodiments the phenylalanine 4-hydroxylase may be a full-length or truncated recombinant phenylalanine 4-hydroxylase. Also, the phenylalanine 4-hydroxylase may be mammalian. For example, the phenylalanine 4-hydroxylase may be human enzyme. In addition the phenylalanine 4-hydroxylase may be thiolated in a serine/threonine/tyrosine-rich region. Particularly, the thiol may be near the serine-16 amino acid.

In another embodiment of the present invention there is provided a method for increasing therapeutic activity of phenylalanine 4-hydroxylase in a subject suffering from phenylketonuria, the method comprising administering one or more of a thiolated recombinant phenylalanine 4-hydroxylase or a phenylalanine ammonia lyase to the subject under conditions effective to deliver the thiloated recombinant phenylalanine 4-hydroxylase and/or phenylalanine ammonia lyase to the subject's small intestine.

Further to this embodiment the method comprises administering a peptidase as described supra. The peptidase also is as described supra. Also, the peptidase and/or the thiolated phenylalanine 4-hydroxylase and/or the phenylalanine ammonia lyase may be formulated as described supra. Also, the formulations may be formulated for a timed-release as described supra. In addition the thiolated phenylalanine 4-hydroxylase is as described supra.

In yet another embodiment of the present invention there is provided an oral dosage form comprising one or more cores comprising one or both of a phenylalanine 4-hydroxylase or a phenylalanine ammonia lyase; and an enteric coating on the one or more cores. Further to this embodiment the oral dosage form comprises a peptidase such as described supra. In both embodiments the phenylalanine 4-hydroxylase may be a recombinant enzyme and/or thiolated, as described supra. Also, the oral dose form may be a time-release form.

Provided herein are methods and oral formulations for treating a subject suffering from phenylketonuria. The method includes administering a phenylalanine hydroxylase (PAH) and/or a phenylalanine lyase (PAL) to the subject under conditions effective to deliver the phenylalanine 4-hydroxylase and/or phenylalanine lyase to the subject's small intestine. This can be achieved in a number of ways. For example, the phenylalanine 4-hydroxylase and/or phenylalanine lyase can be administered by direct injection into the subject's small intestine. Alternatively, the phenylalanine 4-hydroxylase and/or phenylalanine lyase can be administered directly to the subject's small intestine via a permanently, semi-permanently, or temporarily placed tube that is in communication with the small intestine. Examples of such tubes include duodenal tubes, jejunostomy tubes, and the like, as well as tubes that are commonly used for nasoenteric intubation, e.g., for duodenal, jejunal, and/or ileal delivery.

Alternatively, the phenylalanine 4-hydroxylase and/or phenylalanine lyase can be delivered to the subject's small intestine by formulating the phenylalanine 4-hydroxylase and/or phenylalanine lyase with an enteric coating and orally administering the enterically coated phenylalanine 4-hydroxylase and/or phenylalanine lyase to the subject. The enterically coated phenylalanine 4-hydroxylase and/or phenylalanine lyase can, for example, be provided in a dosage form that includes (i) a core containing phenylalanine 4-hydroxylase and/or phenylalanine lyase, and (ii) an enteric coating surrounding the core. The term "core" is meant to include not only tablets, pellets, beads, beadlets, and granules, but also capsules, e.g. soft or hard capsules of gelatine or starch. Such cores can be produced in any conventional manner. Other pharmaceutically acceptable ingredients may be present in the cores, e.g. those conventionally used in the preparation of pharmaceutically compositions, e.g. fillers, e.g. lactose, glidants, e.g. silica, and lubricants, e.g. magnesium stearate.

The enteric coating may be designed to provide for protection of the phenylalanine 4-hydroxylase and/or phenylalanine lyase at a pH less than 3, as found in the stomach, to permit release of the phenylalanine 4-hydroxylase and/or phenylalanine lyase at a pH in a local environment of the small intestine. For example, enteric coating can be designed to permit release of the phenylalanine 4-hydroxylase and/or phenylalanine lyase at a pH that is found in the duodenal portion of the small intestine, at a pH that is found in the jejunal portion of the small intestine, and/or at a pH that is found in the ileal portion of the small intestine. By way of further illustration, the enteric coating can be designed to permit release of the phenylalanine 4-hydroxylase and/or phenylalanine lyase at a pH of greater than about 4.5, about 5, 5.5, 6, 6.5, 7, 7.5, or 8. The enteric coating can be designed to release the phenylalanine 4-hydroxylase and/or phenylalanine lyase rapidly, for example, such that, once release of phenylalanine 4-hydroxylase and/or phenylalanine lyase commences, substantially all, e.g., more than 60%, 70%, 80%, or 90%, etc., of the phenylalanine 4-hydroxylase and/or phenylalanine lyase contained in the dosage form is released in less than 8 hours, such as in less than 7 hours, 6 hours, 5 hours, 4 hours, 3 hours, 2 hours, or 1 hour, etc.

By way of illustration, suitable enteric coatings include those that include one or more polymeric materials which encases a core containing the phenylalanine 4-hydroxylase and/or phenylalanine lyase. Examples of suitable enteric coatings that can be used in the methods of the present invention include those which have no significant dissolution at pH levels below 4.5, no significant dissolution at pH levels below 4, no significant dissolution at pH levels below 3.5, etc. Examples of suitable enterically coated dosage forms that can be used in the methods of the present invention include those which have no significant release of the phenylalanine 4-hydroxylase and/or phenylalanine lyase contained in the dosage form, e.g., less than 50%, such as less than 40%, 30%, 20%, or 10%, etc., release in less than 3 hours, such as in less than 2.5 hours, 2 hours, 1.5 hours, or 1 hour, etc.

Illustratively, to provide a predictable dissolution profile corresponding to the typical human small intestine transit time of about 3 hours and to permit reproducible release therein, the enteric coating can be designed to begin to dissolve at a pH between of about 4.5 and 5.5, which is within the pH range of the duodenum, and to continue to dissolve at the pH range within the small intestine which is up to about 7.2 pH. For example, the amount of enteric coating used can be selected such that the enteric coating is substantially dissolved during the approximate three-hour transit time within the small intestine or the amount of enteric coating used can be selected such that the enteric coating is substantially dissolved well before the approximate three-hour transit time within the small intestine. For example, the enteric coating is substantially dissolved within 30 minutes, 1 hour, 1.5 hours, or 2 hours, etc. of entering the small intestine.

Enteric coatings, suitable for use in the methods of the present invention, include enteric coating polymers known in the art, for example, hydroxypropyl methylcellulose phthalate (HPMCP-HP50, USP/NF 220824 HPMCP-HP55, USP/NF type 200731 and HP55S; Shin Etsu Chemical), polyvinyl acetate phthalate (COATERIC™; Colorcon Ltd.), polyvinyl acetate phthalate (SURETERIC™; Colorcon, Ltd.), and cellulose acetate phthalate (AQUATERIC™; FMC Corp.), and the like. The enteric coating can include a methacrylic acid copolymer, such as in the case where the methacrylic acid copolymer is an aqueous acrylic resin dispersion. By way of further illustration, the enteric coating can use an anionic copolymer derived from methacrylic acid and ethyl acrylate, for example, having a ratio of free carboxyl groups to the ester of approximately 1:1 and/or having a mean molecular weight of approximately 250,000. One such anionic copolymer is supplied as in aqueous dispersion containing 30% w/w of dry lacquer substance by Rohm-Pharma Co., Germany (EUDRAGIT™ L30D-55).

Certain enteric coating materials known in the art are acidic in nature and may cause chemical degradation of an acid labile actives when in direct contact with the active. This can be especially true under the high temperature and humidity conditions experienced during aqueous enteric coating processes. To reduce this acid-caused degradation, a protective coat or subcoat can be applied to the particles, beadlets, pellets, etc. prior to applying an enteric coating. This protective coat physically separates the acid labile active from the enteric coating and may be useful for improving the stability of the active. To further reduce this problem, the enteric coating polymer can be chosen so as to have a pH, e.g., a pH of about 4.5 or higher, or of about 5 or higher, etc., which does not cause significant degradation of any acid labile actives contained within the core.

When using an acidic enteric coating polymer, the pH of the acidic enteric coating polymer can be raised by using a suitable alkalizing agent, e.g., sodium hydroxide, to a point which is below the pH wherein the enteric integrity of the polymer could be lost. This partial acid neutralization can be used to provide a more stable composition for any acid labile actives contained in the core. By using this partial acid neutralization method, the incompatibility between the acid labile active and the enteric coating can be reduced to a degree such that a protective subcoat between the active and the enteric coating is not necessary to reduce acid degradation of the core. The partial acid neutralization method allows for the quicker release of the medicament, since a subcoat layer can delay drug release and since the pH of the enteric coating will only have to be slightly raised to result in the breakdown of the enteric coating. The enteric coating can also contain a plasticizer. Examples of suitable plasticizers include triethyl citrate (Citroflex-2), diethyl phthalate, triacetin, tributyl sebecate, and polyethylene glycol.

The amount of enteric coating employed will depend on a number of factors, e.g., on the desired time release profile, on the nature of the material(s) used to make the enteric coating, and on whether a subcoat is used, etc. For example, the weight of enteric coating used can be from about 5% to about 30% of the weight of the core. By way of illustration, the enteric coating can include methacrylic acid copolymer, for example, in an amount of approximately 5% to 30%, preferably, approximately 10% to 20%, by weight and plasticizer, for example, in an amount of approximately 1% to 6%, preferably, approximately 2% to 3%, by weight. These weights are based on total concentration of solids in the enteric coating solution/suspension.

The enteric coating material can be provided on the surface of the dosage form, e.g., an enterically coated tablet in which the enteric coating material surrounds a single core that contains the phenylalanine 4-hydroxylase and/or phenylalanine lyase. Alternatively, the enteric coating material can be used in a microencapsulation process, for example, in which the enteric coating material is used to coat the surfaces of a plurality of phenylalanine 4-hydroxylase and/or phenylalanine lyase-containing cores where the plurality of enterically coated cores being packaged in a capsule or other such dosage form.

By way of further illustration, suitable enteric coatings can include any pharmaceutically acceptable coating that prevents the release of the active agent (phenylalanine 4-hydroxylase and/or phenylalanine lyase) in the stomach and that disintegrate sufficiently in the intestine tract by contact with approximately neutral or alkaline intestine juices to allow release of the active agent (phenylalanine 4-hydroxylase and/or phenylalanine lyase) into the small intestine. Various in vitro tests for determining whether or not a coating is classified as an enteric coating have been published in the pharmacopoeia of various countries.

The thickness of the enteric coating can vary and depends, inter alia, on its permeability in water and acids. The enteric coating can be about 16-30 mg, e.g. 16-20 mg or 16-25 mg on a size 1 gelatine capsule. Similar thicknesses may be applied in other formulations. Illustratively, suitable enteric coatings include those of 5-100 µm, such as 20-80 µm thickness.

The coating can be suitably selected from macromolecular polymers as are known and standard in the art (5-8). Suitable polymers include, but are not limited to, cellulose ester derivatives, cellulose ethers, acrylic resins, such as methylacrylate copolymers and copolymers of maleic acid and phthalic acid derivatives. By way of further illustration, enteric coating films can be made from cellulose acetate phthalate and trimellitate, from methacrylic acid copolymers, e.g. copolymers derived from methylacrylic acid and esters thereof, containing at least 40% methylacrylic acid, and from-hydroxypropyl methylcellulose phthalate.

Methylacrylates include those of molecular weight above 100,000 daltons based on, e.g. methylacrylate and methyl or ethyl methylacrylate in a ratio of about 1:1. Suitable methylacrylates include Endragit L, e.g. L 100-55, (Rohm GmbH, Darmstadt, Germany). Suitable cellulose acetate phthalates include those having an acetyl content of 17-26% and a phthalate content of from 30-40% with a viscosity of ca. 45-90 cP. Suitable cellulose acetate trimellitates include those having an acetyl content of 17-26%, a trimellityl content from 25-35% with a viscosity of ca. 15-20 cS. An example of an suitable cellulose acetate trimellitate is the marketed product CAT (Eastman Kodak Company, USA). Suitable hydroxypropyl methylcellulose phthalates include those having a molecular weight of from 20,000 to 100,000 daltons e.g. 80,000 to 130,000 daltons, e.g. a hydroxypropyl content of from 5 to 10%, a methoxy content of from 18 to 24% and a phthalyl content from 21 to 35%. An example of an appropriate cellulose acetate phthalate is the marketed product CAP (Eastman Kodak, Rochester N.Y., USA). Examples of suitable hydroxypropyl methylcellulose phthalates include the marketed products having a hydroxypropyl content of from 6-10%, a methoxy content of from 20-24%, a phthalyl content of from 21-27%, a molecular weight of about 84,000 daltons known under the trade mark HP50 and available from Shin-Etsu Chemical Co. Ltd., Tokyo, Japan. Other examples of suitable hydroxypropyl methylcellulose phthalates include the marketed products and having a hydroxypropyl content, a methoxy content, and a phthalyl content of 5-9%, 18-22%, and 27-35% respectively, and a molecular weight of 78,000 daltons, known under the trademark HP55 and available from Shin-Etsu Chemical Co. Ltd., Tokyo, Japan.

The enteric coating can be carried out in a conventional manner, e.g., so that the cores are sprayed with a solution of the enteric-coating. Suitable solvents for the enteric-coating are, for example, organic solvents, e.g. an alcohol, e.g., ethanol, a ketone, e.g., acetone, halogenated hydrocarbons, e.g., $CH_2Cl_2$), or mixtures of such solvents, e.g. ethanol/acetone at, for example, 1:1 to 10:1. A softener, such as di-n-butylphthalate or triacetin, can be added to such a solution, e.g. in a ratio of coating material to softener of from about 1:0.05 to about 1:0.3. If desired for cellulose phthalates and other acidic coating materials, an ammonium salt may be found and an aqueous solution may be used. A fluidized bed coater may be used for coating.

In one illustrative embodiment, the cores are treated at room temperature or warmed up to 40° C., e.g., by warm air of 40° up to 70° C., before spraying. To avoid a sticking of the cores, the spray procedure can be interrupted at certain time intervals and the cores then warmed up again. It is, however, also possible to proceed without interruption of the spray procedure, e.g., by automatic regulation of the spray amount taking into account the temperature of exhaust air and/or cores. The spray pressure may vary within wide ranges. Suitable spray pressures include those of from about 1 to about 1.5 bar. Further details regarding the selection, preparation, and application of enteric coatings are available in the literature (5-8).

It should be noted that a portion of the phenylalanine 4-hydroxylase and/or the phenylalanine lyase that is administered to the subject can be delivered to other segments of the subject's gastrointestinal tract, e.g., the subject's stomach, provided that a significant portion of the phenylalanine 4-hydroxylase and/or the phenylalanine lyase is delivered to the subject's small intestine. It is believed that the acidic environment of the stomach destroys or significantly reduces the activity of phenylalanine 4-hydroxylase and/or phenylalanine lyase, and, thus, any phenylalanine 4-hydroxylase and/or phenylalanine lyase that is released into the stomach is destroyed or otherwise rendered inactive.

Irrespective of how phenylalanine 4-hydroxylase and/or phenylalanine lyase is delivered to the subject's small intestine, e.g., whether it be by direct administration to the small intestine via injection or a tube or whether it be via an enterically coated, orally administered dosage form, the method of the present invention can, optionally, further include administering a peptidase to the subject under conditions effective to deliver the peptidase to the subject's stomach and/or small intestine. In cases where the peptidase is acid-stable, it can be delivered to the stomach or to the small intestine. In the case where the acidic conditions of the stomach would destroy or significantly reduce the activity of the peptidase, delivery to the small intestine is preferred.

The peptidase can be administered sequentially with the phenylalanine 4-hydroxylase and/or phenylalanine lyase, where the peptidase is administered prior to administering the phenylalanine 4-hydroxylase and/or phenylalanine lyase, e.g., from 5 minutes to about 2 hours before, or where the peptidase is administered after administering the phenylalanine 4-hydroxylase and/or phenylalanine lyase, e.g., from about 5 minutes to about 2 hours after. Alternatively, the peptidase can be administered concurrently with the phenylalanine 4-hydroxylase and/or phenylalanine lyase where the peptidase is administered simultaneously with the phenylalanine 4-hydroxylase and/or phenylalanine lyase or at substantially the same time as the phenylalanine 4-hydroxylase and/or phenylalanine lyase, e.g., where the peptidase and the phenylalanine 4-hydroxylase and/or phenylalanine lyase are administered within 5 minutes of one another. In cases where the peptidase is administered concurrently with the phenylalanine 4-hydroxylase and/or phenylalanine lyase, the peptidase can be administered with the phenylalanine 4-hydroxylase and/or phenylalanine lyase in separate formulations, or the peptidase can be administered with the phenylalanine 4-hydroxylase and/or phenylalanine lyase in a single formulation, e.g., in a single, enterically coated formulation. In cases where the peptidase is administered with the phenylalanine 4-hydroxylase and/or phenylalanine lyase in a single dosage form, the dosage form can be formulated (i) so as to deliver the peptidase to the stomach and the phenylalanine 4-hydroxylase and/or phenylalanine lyase to the small intestine; (ii) so as to deliver the peptidase to the small intestine and the phenylalanine 4-hydroxylase and/or phenylalanine lyase to the small intestine; (iii) so as to deliver the peptidase to one portion of the small intestine, e.g., the duodenum, and the phenylalanine 4-hydroxylase and/or phenylalanine lyase to a different portion of the small intestine, e.g., the jejunum, etc.

The present invention also provides an oral dosage form or formulation that includes a phenylalanine 4-hydroxylase and/or a phenylalanine lyase. The oral dosage form is formulated so as to deliver the phenylalanine 4-hydroxylase and/or phenylalanine lyase to a subject's small intestine. Examples of suitable phenylalanine 4-hydroxylase and phenylalanine lyase for use in the oral dosage forms of the present invention include those discussed hereinabove.

The oral dosage form can be enterically coated so as to deliver the phenylalanine 4-hydroxylase and/or phenylalanine lyase to the small intestine. Details regarding enteric coatings and methods for preparing enterically coated, phenylalanine 4-hydroxylase and/or phenylalanine lyase-containing oral dosage forms are set forth hereinabove. The oral dosage form may be enterically coated, for example, where the oral dosage form includes a single phenylalanine 4-hydroxylase and/or phenylalanine lyase-containing core that is enterically coated. The oral dosage form may be an enterically coated capsule that contains phenylalanine 4-hydroxylase and/or phenylalanine lyase, e.g., in the form of granules, powder, suspension, etc. The oral dosage form may contain a plurality of phenylalanine 4-hydroxylase and/or phenylalanine lyase-containing cores, each of which is enterically coated, the plurality of enterically coated cores being packaged in a capsule or other such dosage form.

The oral dosage form of the present invention can further include a peptidase. Examples of suitable peptidases and methods for formulating such dosage forms include those that have been described hereinabove. The oral dosage form can be formulated to deliver the peptidase to the subject's stomach, to the subject's small intestine, or to both. The peptidase in the oral dosage form is enterically coated, for example, where the oral dosage form includes a single core containing both the peptidase and the phenylalanine 4-hydroxylase and/or phenylalanine lyase that is enterically coated and where the oral dosage form is an enterically coated capsule that contains the peptidase and the phenylalanine 4-hydroxylase and/or phenylalanine lyase, e.g., in the form of granules, powders, suspensions, etc.

The phenylalanine 4-hydroxylase and/or phenylalanine lyase and the peptidase may be enterically coated, for example, where the oral dosage form includes a single core containing both the peptidase and the phenylalanine 4-hydroxylase and/or phenylalanine lyase that is enterically coated. The oral dosage form may have a plurality of cores containing both the peptidase and the phenylalanine 4-hydroxylase and/or phenylalanine lyase, each of which cores is enterically coated and the plurality of enterically coated cores are packaged in a capsule or other such dosage form. The oral dosage form may contain a plurality of cores, some of which contain the peptidase and others of which contain the phenylalanine 4-hydroxylase and/or phenylalanine lyase such that each of the cores is enterically coated and the plurality of enterically coated cores are packaged in a capsule or other such dosage form, etc. Alternatively, the phenylalanine 4-hydroxylase and/or phenylalanine lyase are enterically coated and the peptidase is not enterically coated, for example, where the oral dosage form contains a plurality of phenylalanine 4-hydroxylase and/or phenylalanine lyase-containing cores that are enterically coated and a plurality of peptidase-containing cores that are not enterically coated and the plurality of enterically coated cores and non-enterically coated cores are packaged together in a single capsule or other such dosage form.

The present invention relates to a method for increasing the activity of a phenylalanine hydroxylase. The method includes thiolating a serine/threonine/tyrosine-rich region of the phenylalanine hydroxylase. The present invention also relates to a phenylalanine 4-hydroxylase that is thiolated in a serine/threonine/tyrosine-rich region of the phenylalanine hydroxylase, for example, near the phenylalanine hydroxylase's serine-16 amino acid residue. Suitable procedures for the thiolation of phenylalanine 4-hydroxylase include those that are similar to the techniques have been described in (9), which is hereby incorporated by reference.

The following examples are given for the purpose of illustrating various embodiments of the invention and are not meant to limit the present invention in any fashion.

EXAMPLE 1

Thiophosphorylation of PAH

The reaction requires protein (10.4 mg/ml), buffer (15 mM Na-HEPES, pH 7.0, 3 mM dithiothreitol, 0.03 mM EDTA), 500 nM ATP gamma S (prepare 2 mM=2.18 mg in 2 ml buffer). 500 mM ATP, SDS Page or urea gel, and 200 nM protein kinase A (Upstate Biotechnology).
Protocol Wild-type human phenylalanine hydroxylase (wt-hPAH) in 15 mM Na-HEPES, pH 7.0, 3 mM dithiothreitol, 0.03 mM EDTA, 0.1 mM EGTA, and 10 mM magnesium acetate is prepared. 200 nM of PKA subunit catalytic subunit is added. Initiate the reaction by adding 500 nM of ATPgamma-S and incubate at 30° C. for 2-4 mins. A parallel reaction is run as above except that the reaction is initiated by adding 500 nM of ATP. The protein is concentrated by passing through YM10. Both a standard protein assay and a standard enzyme assay are performed.

EXAMPLE 2

Recombinant PAH (dt-hPAH) Expression and Purification:
Expression of dt-hPAH 2 ml of LB medium containing 50 ug/ml of ampicillin is inoculated with the BL21 (DE3) for 2-3 hrs at 37° C. until the OD at $A_{600}$ reaches 0.8. 1 ml of the cells is transferred into 12 L of LB medium containing 50 ug/ml of ampicillin. The cells are grown overnight at 37° C. The stock is maintained in 25% glycerol. Check that the OD at $A_{600}$ is about 0.8. Add 0.5 mM IPTG for 2-3 hrs to the medium to induce expression. Spin the cells in a large centrifuge, 10,000 g for about 10 mins. After the cells form a pellet, pour out the supernatant and scrape out the cells into a plastic bag. Flatten them into a "pancake" and freeze them at 80° C.
Cell Lysis The buffer is 10 mM Tris-HCl, pH 7.4, 200 mM NaCl, 1 mM EDTA, and 0.2 mM PMSF. Resuspend the pellet in the 300 ml lysis buffer. Sonicate for 20-30 minutes. Set at 70% and sonicate for 1 sec on and 3 secs off for a sonication time of 3 minutes with a total time of 12 mins. Have the cells on ice while resuspending and sonicating. The crude extract is than centrifuged at 98000 g at 4° C. for 10 mins and the supernatant is processed immediately or frozen at −80° C. until used.
Purification of the Lysate All chromatography steps are done at 4° C. The Buffer T is the same as used for cell lysis. Buffer E contains 10 mM Tris-HCl, pH 7.4, 200 mM NaCl, and 1 mM EDTA. Buffer S contains 10 mM Tris-HCl, pH 7.4, 200 mM NaCl, 1 mM EDTA, and 10 mM Maltose. The column is amylose resin. Dilute the protein with Buffer T to reduce the concentration to 3 mg/ml before application to amylose column (2.5 cm×10 cm); this depends on the amount of protein. Pre-equilibrate the column with Buffer E. Wash the column with 40 column volume of buffer E. Elute with Buffer S. Collect 1 ml fraction and pool fractions.
Cleavage with Restriction Protease Factor Xa The pooled fractions are concentrated to a volume of less than 5 ml. Measure protein concentration at 280 nm or with pierce protein assay or Bradford assay. Digest the protein with Factor Xa (1:300) for 4 hrs at 4° C.
Size Exclusion Chromatography A Superdex 200 HR column (1.6 cm×60 cm) is used. Buffer N contains 20 mM Na-Hepes and 0.2M NaCl, pH 7.0 (freshly prepared and degassed). Equilibrate the column with Buffer N at flow rate of 0.38 ml/min. Load the protein and elute with buffer N. Collect 1 ml fractions.

EXAMPLE 3

Phenylalanine Hydroxylase Digestion

In a basic environment, pH 8.5, of the GI tract, a mammalian phenylalanine 4-hydroxylase enzyme (human or mouse) expressed recombinantly in *E. Coli* is stable for up to 24 hours at pH 8.5. The recombinant enzyme can be full length or truncated. When the hydrolytic enzymes trypsin and chymotrypsin are added to the recombinant phenylalanine 4-hydroxylase or its conjugates in a test tube at pH 8.5, the enzyme half-life is 6 hours.

This result indicates that, if the recombinant phenylalanine 4-hydroxylase enzyme is taken in an enteric coated formulation, it will be sufficiently stable to convert phenylalanine to tyrosine in the GI tract, before the phenylalanine can be absorbed into the bloodstream. This will lower the Phe levels in the blood, constituting a treatment for PKU. Table 1 compares the activity of phenylalanine 4-hydroxylase in the presence of trypsin and chymotrypsin with that of phenylalanine 4-hydroxylase alone.

TABLE 1

| time (min) | PAHTC (units/mg) | PAH (units/mg) |
|---|---|---|
| 0 | 488.14 | 548.12 |
| 30 | 501.03 | 488.18 |
| 60 | 448.80 | 474.49 |
| 120 | 278.42 | 489.90 |
| 240 | 197.09 | 458.22 |
| 360 | 227.05 | 435.96 |
| 600 | ND | ND |
| 1440 | 171.40 | 403.42 |

The data for the proteolysis are given in Table 2 and graphed in FIG. 1. It can be concluded that MBP-phenylalanine 4-hydroxylase in the presence of trypsin and chymotrypsin (MBPTC) is stable up to 6 hours, but there is no activity after overnight incubation. Phenylalanine hydroxylase (PAHTC) loses activity after 15 minutes, but regains some activity after 4 hours. It is possible that the fragment may have some activity which increases up to 6 hours. No activity after overnight incubation. Phenylalanine hydroxylase without trypsin and chymotrypsin seems to maintain its activity even after overnight incubation. The tube at 6 hours was broken and lost.

TABLE 2

| time (min) | PAH (units/mg) | PAHTC (units/mg) | MBPTC (units/mg) |
|---|---|---|---|
| 0 | 494.18 | 668.84 | 621.75 |
| 15 | 661.99 | 384.59 | 625.17 |
| 30 | 488.18 | 411.13 | 629.45 |
| 60 | 697.09 | 318.66 | 622.60 |
| 240 | 592.64 | 525.86 | 634.59 |
| 360 | Tube Lost | 582.36 | 627.74 |
| 1440 | 621.75 | 236.47 | 233.05 |

EXAMPLE 4

In vivo Effect of Enteric Coated PAH on Phe and Tyr Levels

Figure 2A:
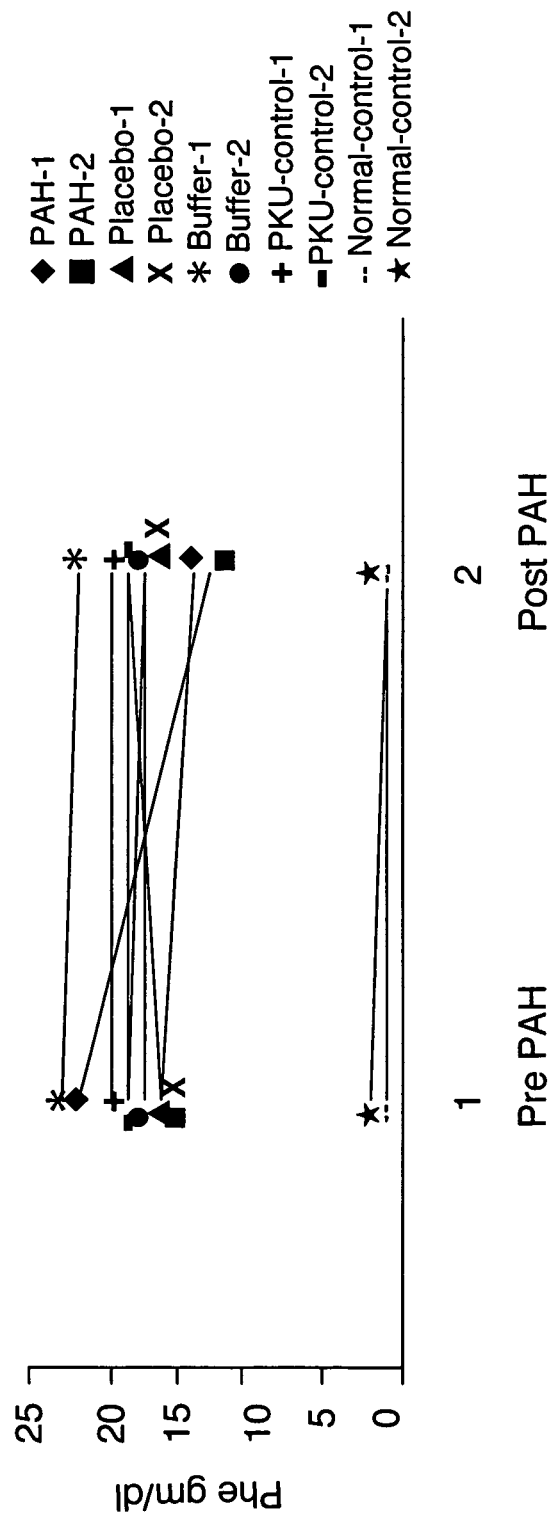
FIGS. 2A-2B illustrate graphically the blood levels of phenylalanine (FIG. 2A) and tyrosine (FIG. 2B) in phenylketonuric mice fed enterically-coated pellets of phenylalanine hydroxylase.
Figure 2B:
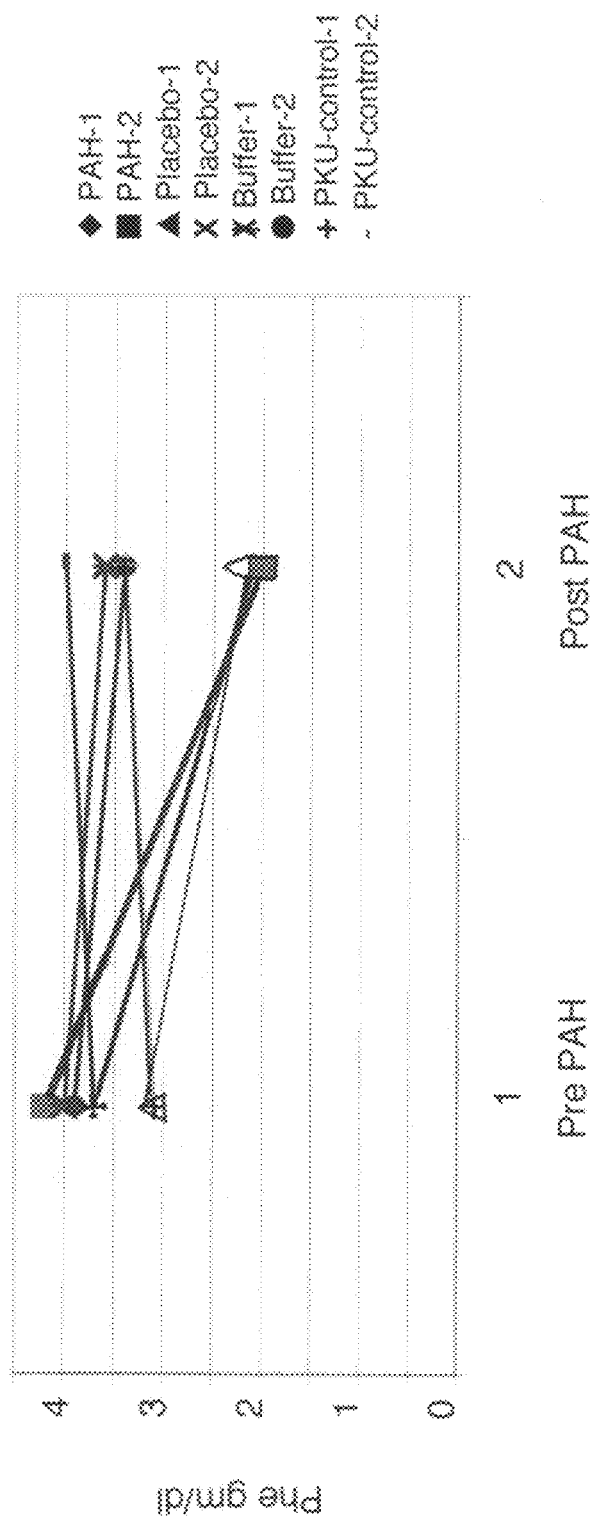

Recombinant human phenylalanine 4-hydroxylase was prepared as described providing 290 mg of phenylalanine hydroxylase. Tiny pellets of the enzyme were coated to 0.4-0.5 mm, so they can travel through the mouse esophagus. Each pellet contained approximately 0.5 mg of enzyme. Since the mice are nocturnal, the enzyme pellets were given in the morning and one dose was given in the evening. Placebo pellets of the same size were used as control. Also, as controls, mice were fed a buffer. Each mouse was given the pellets for three days, in a dose of approximately 10 mg per feeding. Blood phenylalanine (FIG. 2A) and tyrosine (FIG. 2B) were determined daily from the tail blood in the phenylalanine hydroxylase-fed mice, placebo-fed mice, buffer-fed mice and in normal control mice and PKU control mice. Tables 3 and 4 show the 3-day average blood levels of phenylalanine and tyrosine.

TABLE 3

Phenylalanine

| Mice | Pre-PAH | Post-PAH | Percent | % Drop |
|---|---|---|---|---|
| PAH-1 | 20.41 | 13.66 | 64.5 | 35.5 |
| PAH-2 | 15.985 | 12.47 | 78.03 | 21.97 |
| Placebo-1 | 17.74 | 16.47 | 92.84 | 7.16 |
| Placebo-2 | 15.36 | 16.01 | 104.2 | −4.2 |
| Buffer-1 | 21.705 | 21.03 | 96.8 | 3.2 |
| Buffer-2 | 16.685 | 16.13 | 96.7 | 3.3 |
| PKU-control-1 | 18.86 | 18.26 | 96.8 | 3.2 |
| PKU-control-2 | 17.72 | 16.84 | 95.03 | 4.97 |
| Normal-control-1 | 1.155 | 1.15 | 100 | |
| Normal-control-1 | 2.13 | 1.11 | 100 | |

TABLE 4

Tyrosine

| Mice | Pre-PAH | Post-PAH |
|---|---|---|
| PAH-1 | 0.37 | 0.21 |
| PAH-2 | 0.42 | 0.2 |
| Placebo-1 | 0.31 | 0.23 |
| Placebo-2 | 0.37 | 0.36 |
| Buffer-1 | 0.40 | 0.36 |
| Buffer-2 | 0.39 | 0.34 |
| PKU-control-1 | 0.31 | 0.34 |
| PKU-control-2 | 0.37 | 0.4 |

The following references are cited herein.
1. Pardridge, "Blood-Brain Barrier Amino Acid Transport: Clinical Implications," chapter 6 in Inborn Errors of Metabolism in Humans, Cockburn et al., eds, Lancaster, England: MTP Press Ltd. (1980)
2. Kaufman, 1998, J. Inher. Metab. Dis., 21 (Supp 3):4-19.3.
3. Lou, 1983, Lancet, 2:150-151.
4. Berry et al., 1990, Am. J. Dis. Child., 144:539-543.
5. Lachman et al., The Theory and Practice of Industrial Pharmacy, 3rd ed., 1986, pp. 365-373.
6. Sucker et al., Pharmazeutische Technologie, Thieme, 1991, pp. 355-359.
7. Hagers Handbuch der Pharmazeutischen Praxis, 4th ed., vol. 7, pp. 739-742 and 766-778, Springer Verlag, 1971.
8. Remington's Pharmaceutical Sciences, 13th ed., pp. 1689-1691, Mack Publ., Co., 1970.
9. Miranda et al., 2002, Journal of Biological Chemistry, 277(43):40937-40943.

Any patents or publications mentioned in this specification are indicative of the level of those skilled in the art to which the invention pertains. Further, these patents and publications are incorporated by reference herein to the same extent as if each individual publication was specifically and individually incorporated by reference.

Although preferred embodiments have been depicted and described in detail herein, it will be apparent to those skilled in the relevant art that various modifications, additions, substitutions and the like can be made without departing from the spirit of the invention, and these are therefore considered to be within the scope of the invention as further illustrated by the claims which follow.

What is claimed:

1. An oral dosage form comprising:
   (a) phenylalanine 4-hydroxylase and/or phenylalanine ammonia lyase; and
   (b) at least one dipeptidase.

2. The oral dosage form of claim 1, further comprising one or more cores comprising the phenylalanine 4-hydroxylase and/or phenylalanine ammonia lyase, wherein one or more cores have an enteric coating.

3. The oral dosage form of claim 1, wherein the dipeptidase is enterically-coated.

4. The oral dosage form of claim 2, wherein both (a) the phenylalanine 4-hydroxylase and/or phenylalanine ammonia lyase containing core, and (b) the dipeptidase are enterically coated.

5. The oral dosage form of claim 2, wherein the oral dosage form is a time-release oral dosage form.

6. The oral dosage form of claim 1, wherein the phenylalanine 4-hydroxylase is a full-length or truncated recombinant phenylalanine 4-hydroxylase.

7. The oral dosage form of claim 6, wherein the phenylalanine 4-hydroxylase is a mammalian phenylalanine 4-hydroxylase.

8. The oral dosage form of claim 7, wherein the phenylalanine 4-hydroxylase is a human phenylalanine 4-hydroxylase.

9. The oral dosage form of 1, wherein said phenylalanine 4-hydroxylase is thiolated in a serine/threonine/tyrosine-rich region.

10. The oral dosage form of claim 9, wherein the thiol is in a region near serine-16 amino acid.

11. A method for treating a subject suffering from phenylketonuria, said method comprising:
   administering the oral dosage form of claim 1 to the subject having phenylketonuria.

* * * * *